(12) United States Patent
Gamache et al.

(10) Patent No.: US 7,451,634 B2
(45) Date of Patent: Nov. 18, 2008

(54) CHROMATOGRAPHIC METHODS FOR MEASURING IMPURITIES IN A GAS SAMPLE

(75) Inventors: Yves Gamache, Adstock (CA); André Fortier, Adstock (CA)

(73) Assignee: Systeme Analytique Inc., Thetford-Mines, Quebec (CA)

( * ) Notice: Subject to any disclaimer, the term of this patent is extended or adjusted under 35 U.S.C. 154(b) by 112 days.

(21) Appl. No.: 11/361,068

(22) Filed: Feb. 22, 2006

(65) Prior Publication Data
US 2006/0196247 A1 Sep. 7, 2006

Related U.S. Application Data

(60) Provisional application No. 60/654,466, filed on Feb. 22, 2005.

(51) Int. Cl.
*G01N 30/04* (2006.01)
*G01N 30/46* (2006.01)
*G01N 30/88* (2006.01)

(52) U.S. Cl. ............... 73/23.42; 73/23.35; 73/23.41
(58) Field of Classification Search ............ 73/23.35, 73/23.41, 23.42
See application file for complete search history.

(56) References Cited

U.S. PATENT DOCUMENTS

| | | | |
|---|---|---|---|
| 3,425,807 A | 2/1969 | Levy | |
| 4,271,697 A * | 6/1981 | Mowery, Jr. | ............... 73/61.52 |
| 4,536,199 A | 8/1985 | Toon | |
| 4,780,116 A | 10/1988 | Cheh et al. | |
| 5,152,176 A | 10/1992 | Bryselbout et al. | |
| 5,360,467 A | 11/1994 | Ketkar et al. | |
| 6,000,274 A * | 12/1999 | Lai et al. | ............... 73/23.35 |
| 6,341,520 B1 | 1/2002 | Satoh et al. | |
| 6,474,136 B1 | 11/2002 | Nishina et al. | |
| 2004/0182134 A1* | 9/2004 | Staphanos et al. | ......... 73/23.35 |
| 2004/0234414 A1* | 11/2004 | Bezzola | ............... 422/54 |

FOREIGN PATENT DOCUMENTS

WO   WO 2004/083848   9/2004

* cited by examiner

*Primary Examiner*—Daniel S Larkin
(74) *Attorney, Agent, or Firm*—Darby & Darby PC

(57) ABSTRACT

An improved chromatographic method for measuring impurities in a gas sample that allows extraction of a peak of impurity masked by the sample background. An impurity peak is extracted from the sample background and put in a second sample loop and the second sample loop volume is injected into a second separation column. A "slice" is taken from the sample background to fill the second sample loop and the "slice", whose width is preferably substantially equal to the impurities peak width, is injected into the second separation column. Another embodiment allows concentration of a predetermined impurity, thereby providing an improved precision on the results. The chromatographic method provides an improved measure of argon in oxygen, oxygen in argon and oxygen in hydrogen.

18 Claims, 13 Drawing Sheets

PRIOR ART

CHROMATOGRAPHIC METHODS FOR MEASURING IMPURITIES IN A GAS SAMPLE

FIELD OF THE INVENTION

The present invention generally relates to chromatographic methods for fluid analytical systems, and more particularly concerns an improved chromatographic method for measuring impurities in a gas background. Such a chromatographic method is particularly advantageous when the peak of impurities to be measured is masked by the sample background.

BACKGROUND OF THE INVENTION

In the field of chromatography, it is often necessary to measure impurities in a sample background that is different from the carrier gas used in the system.

Examples of such applications are the measurement of O2 in H2, CO in N2, etc. Many people involved in the art have designed methods or developed separation materials in the attempt of accomplishing such measurements.

A good explanation of the problems involved in such measurements, i.e. separation problems and the resulting detrimental effects on detectors, can be found in U.S. Pat. No. 5,360,467 which describes a method of separating and detecting impurities in using a fractional concentration detector. However, the method they suggest is quite complex to perform and no analytical results are reported.

Thus, the standard way to resolve these issues remains to use a method known as the heartcut method.

In fact, when the sample background is different from the carrier gas, the sample background may interfere with the impurity to be measured by overlapping or masking it. Furthermore, some chromatographic detectors may be overloaded and damaged by the sample background. In such application, the sample background must be first eliminated without affecting the impurities to be measured. The standard method to do this is the heartcut method.

FIG. 1 shows a typical analytical chromatographic system having a valve and column's configuration flowpath that path could be used to achieve this. Indeed, the illustrated heartcut system is provided with one sample loop, two valves V1, V2 and two separation columns. The valve V1 injects the sample loop volume into the first separation column. The function of the first column is to separate as much as possible the sample background from the impurities. The second valve V2 is then actuated in order to vent away the sample background gas eluting from the first column. Before the first peak of interest comes out of the first column, the valve V2 is restored to its original position in order to allow the gas existing the first column to flow into the second column, and then into the detector. In other words, the valve V2 is particularly actuated so as to open a window only for the peak of interest, which then flows into the second column. The second column's function, the analytical one, allows the separation of the impurities as individual peaks. Even with this particular two columns configuration, the sample background gas still produces a large tailing peak that dramatically limits the performance of the system in terms of sensitivity and repeatability. Moreover, in several typical applications, impurity levels are in ppm or ppb range while the sample background is almost 100% pure. Therefore, there is a large difference in the number of molecules between impurities and the sample background. Furthermore, when the elution time of the impurities to be measured comes just after the sample background gas, the standard heartcut method cannot conveniently work. A good example of such situation is the measurement of sub ppm of O2 in H2 background. In this case, even after the H2 heartcut, there is still too much H2 in the second column. FIG. 2 illustrates a typical chromatogram that is obtained with the system shown in FIG. 1. It is clear from FIG. 2, that the heartcut method cannot provide convenient results in this case.

Therefore, it would be desirable to provide an improved chromatographic system and an improved chromatographic method for measuring impurities in a gas sample that would overcome the above mentioned drawbacks of the prior art systems and methods. It would be even more desirable to provide a method that would advantageously allow extracting and measuring a peak of impurities masked by the sample background.

SUMMARY OF THE INVENTION

An object of the present invention is to provide an improved chromatographic method and an improved chromatographic system that satisfy the above mentioned needs.

Accordingly, there is provided a chromatographic method for measuring impurities in a gas sample having a gas background, said method comprising the steps of:

a) providing a chromatographic system having a first sample loop, a first separation column, a second sample loop, a second separation column and a detector serially connected through a plurality of valves, the system being provided with a carrier gas and the gas sample;

b) providing the second sample loop with the carrier gas for purging the second sample loop through a second loop venting line;

c) isolating the second sample loop;

d) providing the first sample loop with the gas sample for filling the first sample loop with a gas sample volume;

e) injecting the gas sample volume into the first column to substantially separate the gas background from the impurities;

f) venting the first column outside the system through a first column vent line for a predetermined venting period of time for eliminating at least a part of the gas background;

g) connecting the first column to the second sample loop during a predetermined filling period of time for filling the second sample loop with a gas mixture comprising a carrier gas volume and a slice of the gas sample volume comprising at least one of the impurities;

h) isolating the second sample loop; and i) injecting the gas mixture into the second column to separate the gas mixture into a plurality of baseline resolved peaks, thereby allowing its measurement of the at least one of the impurities.

The chromatographic method of the present invention advantageously allows to extract a peak of impurity masked by the sample background. Moreover, the chromatographic method advantageously provides an improved measure of argon in oxygen, oxygen in argon and oxygen in hydrogen.

In a further embodiment, the chromatographic system is further provided with an additional detector operatively connectable to the first separation column through a plurality of additional valves, the method further comprising, after the step g), an additional step of connecting the first separation column to the additional detector for measuring the remaining impurities of the gas sample with the additional detector, thereby providing a reduced analysing cycle time of the gas sample.

In another further embodiment, the second sample loop is provided with an additional variable volume, the method further comprising, during step g), the additional steps of:
- measuring a first column gas pressure; and
- expanding the variable volume during filling of the second sample loop according to the first column gas pressure in order to keep constant the gas pressure, advantageously at atmospheric pressure;

and wherein the method further comprises before the step h) the additional steps of:
- isolating an inlet of the second sample loop; and
- reducing the variable volume for pressurizing the second sample loop.

According to another preferred embodiment, before the step h), each of the steps d) to g) are sequentially performed a plurality of times for collecting a plurality of slices of the gas sample volume comprising at least one of the impurities. With this particular embodiment, the method advantageously allows concentration of a predetermined impurity, thereby providing an improved precision on the results.

In another preferred embodiment, the impurities comprise argon and the gas background comprises oxygen, the system being further provided with an O2 trap operatively connectable between the second separation column and the detector through a first and a second additional valves, the method further comprising, after the step i), an additional step of:

j) operatively connecting the O2 trap between the second column and the detector during a predetermined period of time for trapping oxygen therein while providing the detector with a slice of the gas mixture comprising the argon impurities.

BRIEF DESCRIPTION OF THE DRAWINGS

These and other objects and advantages of the invention will become apparent upon reading the detailed description and upon referring to the drawings in which.

While the invention will be described in conjunction with example embodiments, it will be understood that it is not intended to limit the scope of the invention to such embodiments. On the contrary, it is intended to cover all alternatives, modifications and equivalents as may be included as defined by the appended claims.

DESCRIPTION OF PREFERRED EMBODIMENTS

The concept of the present invention advantageously relies on the use of valves whose ports can be independently actuated and whose design provides a tight shut-off or positive sealing action. For example, the diaphragm sealed valve of the same inventors which is described in U.S. patent application Ser. No. 11/064,501 entitled <<Diaphragm-sealed valve, analytical chromatographic system and method using the same>> is particularly well suited to perform the methods of the present invention. The disclosure of this application is incorporated therein in its entirety. The two particularly advantageous features provided by the above mentioned diaphragm sealed valve compared to the other ones of the prior art advantageously allow to envisage a new method that greatly improves over the traditional heartcut methods currently used in the art. It should, however, be mentioned that any other suitable valves could also be used.

Figure 3A:
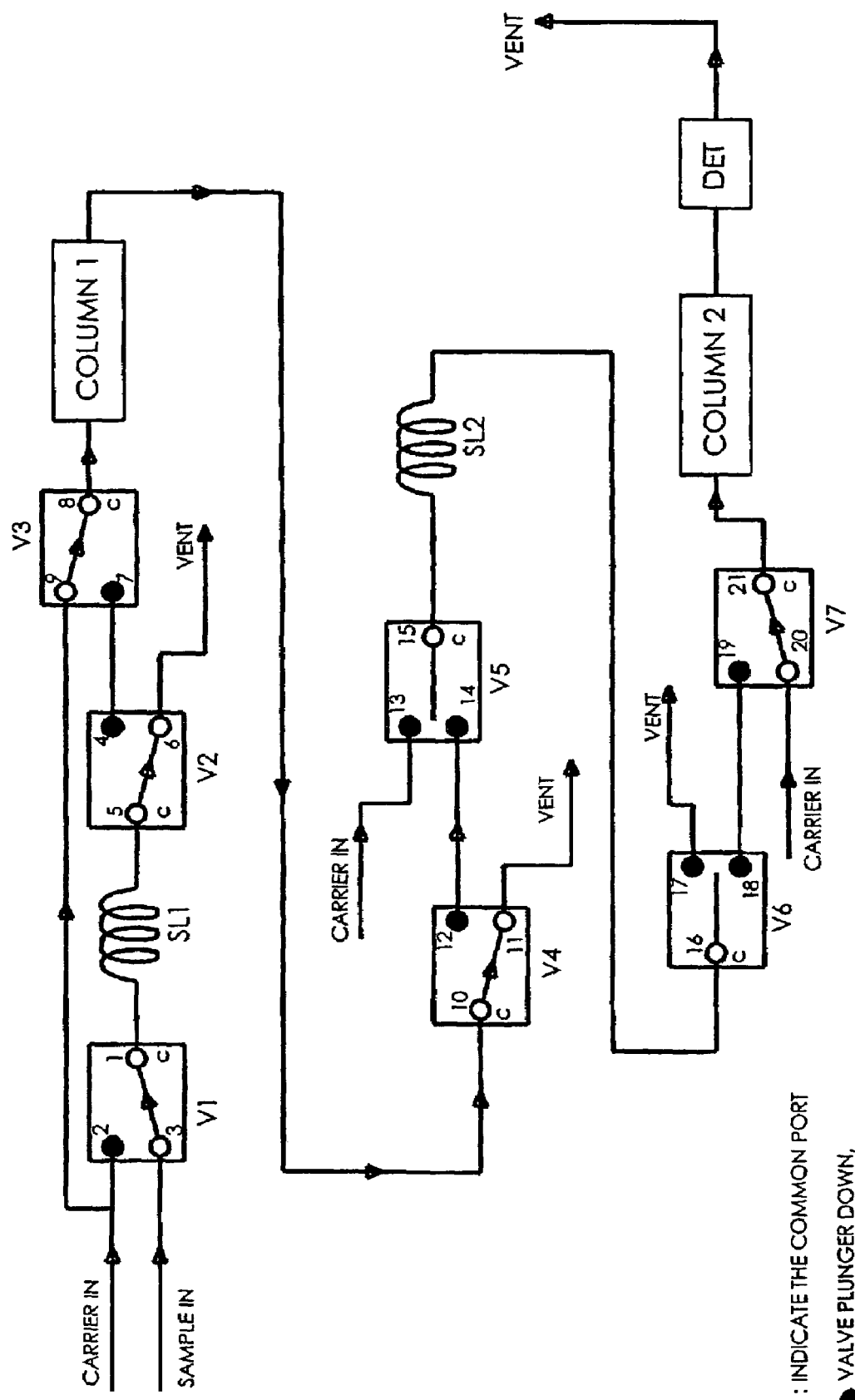
FIG. 3a is a schematic representation of an analytical chromatographic system, according to a preferred embodiment of the present invention, the system being in a first position.
Figure 3B:
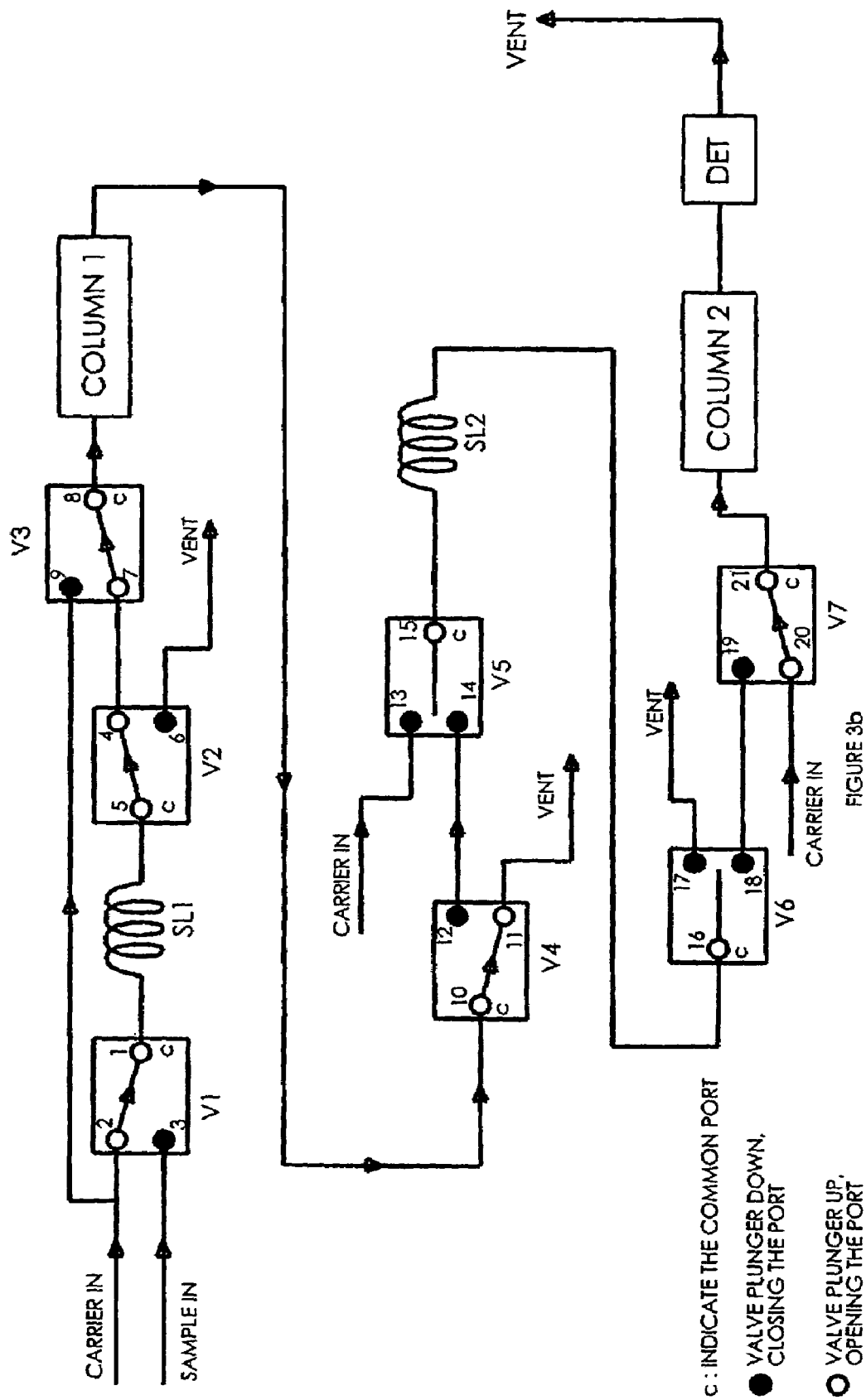
FIG. 3b is another schematic representation of the analytical chromatographic system shown in FIG. 3a, the system being in a second position.

With reference to FIGS. 3a to 3b, which show a preferred embodiment of an analytical chromatographic system of the present invention, the general concept of the present chromatographic method will now be explained. In this system, a plurality of valves, advantageously discrete 3-way basic switching cells, is used to draw the flow path arrangement. Preferably, such valves have independently actuated ports and provide a tight shut-off of the ports. The concept is based on extracting an impurities peak from the sample background and putting it into a second sample loop SL2. Of course, each of a plurality of impurities peaks can advantageously be extracted individually from the sample background and put into the second sample loop SL2. Then, this second sample loop volume is injected into a separation column 2. In fact, the system takes a "slice" from the sample background and fills the second sample loop SL2 with it. Then, the "slice", whose width is advantageously substantially equal to the impurities peak width, is injected into the separation column 2.

Figure 4:
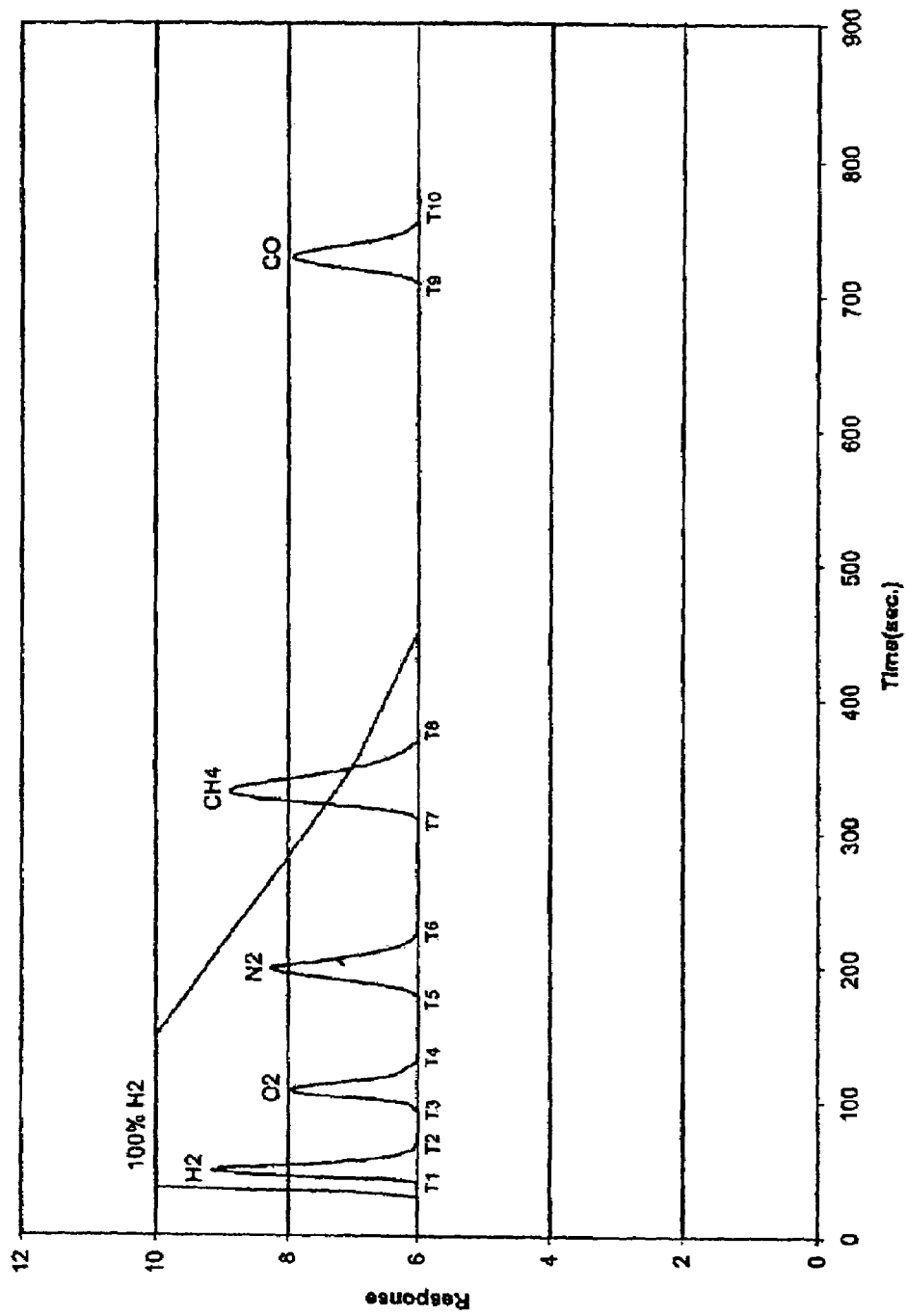
FIG. 4 illustrates typical chromatograms of 0.5 ppm H2-O2-1\12-CH4-CO in argon and 100% H2.

To better illustrate the concept of the present method, reference is now made to FIG. 4. It shows a typical chromatogram obtained with a plasma emission detector using argon as gas carrier when an argon gas sample containing H2, O2, N2, CH4 and CO at about 500 ppb each is injected into a molecular sieve SA separation column. It also shows a typical detector signal when the gas sample injected is 100% H2. The detrimental effect on subsequent impurities is evident. Each of the time indices T1 to T2, T3 to T4, etc. . . . , until T9 to T10 define peak starting and ending time, and therefore the peak width of various impurities for the above mentioned argon gas. In this chromatogram, there is no sample background interference since the sample background is of the same type as the carrier gas. Thus, one can see that all peaks are baseline resolved. This represents the ideal situation. However, in many cases, the gas sample background could also be one of these impurities or a mixture of them. For example, the gas sample background could be H2, O2, N2, etc.

Figure 2:
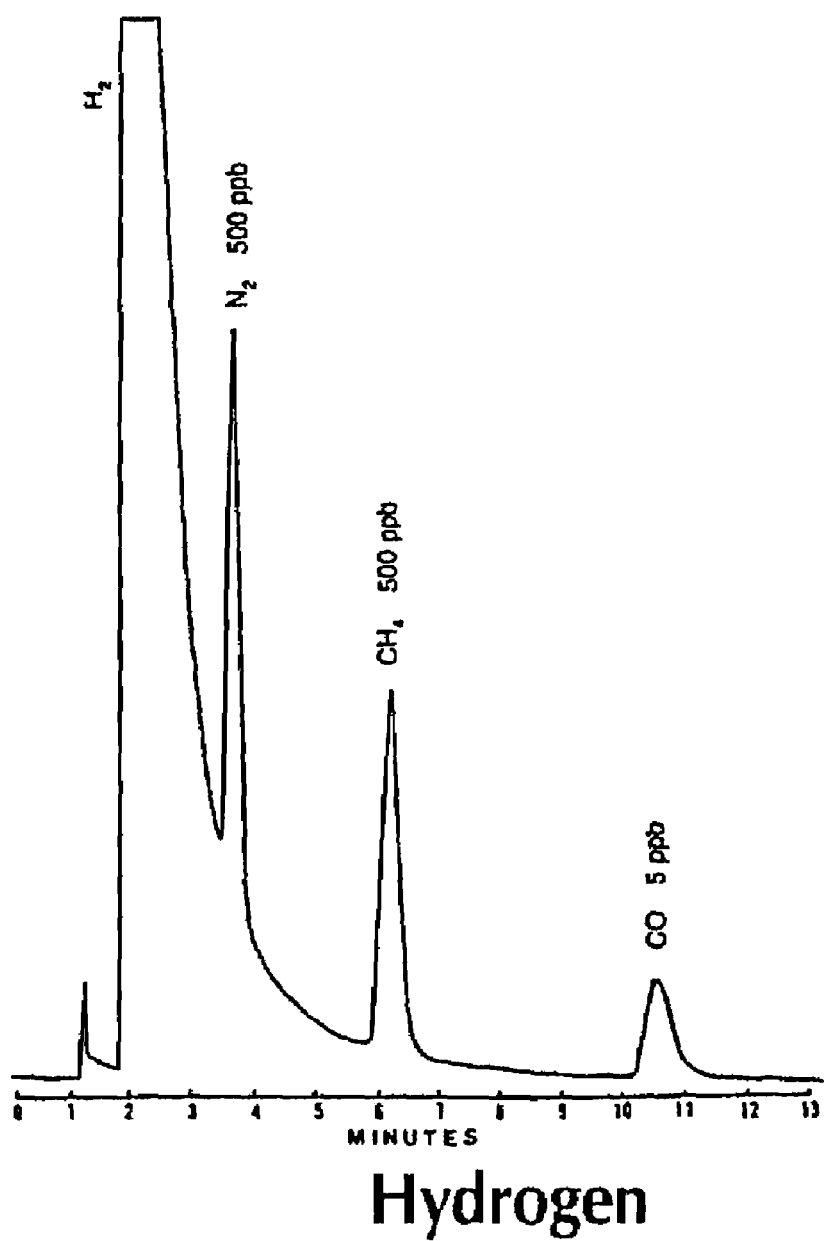
FIG. 2 (PRIOR ART) is a typical chromatogram obtained with the analytical chromatographic system of FIG. 1.

An example of a difficult application as mentioned above is the separation of O2 impurities in an H2 sample. In this case, since the H2 peak is close to O2, the sample background masks the O2 impurities and the detector is driven into saturation by the H2 gas background. Using standard known heartcut method for this application is not enough since the detector sees a large tailing of H2 masking O2 as illustrated in FIG. 2. This problem is well known from people involved in the art. FIG. 4 shows the effect of 100% of H2 as a gas sample. It is clear that O2 and some other impurities will be masked by the H2 gas sample background.

Referring now to FIGS. 3a to 3f, the method for measuring impurities in a gas sample having a gas background according to the present invention will now be described. This chromatographic method advantageously provides an improved measure of argon in oxygen, oxygen in argon and oxygen in hydrogen as non-limitative examples. Firstly, as illustrated on FIG. 3a, the method comprises the step of providing a chromatographic system having a first sample loop SL1, a first separation column 1, a second sample loop SL2, a second separation column 2 and a detector DET serially connected through a plurality of valves. The system is further provided with a carrier gas and the gas sample to be analysed.

Figure 3C:
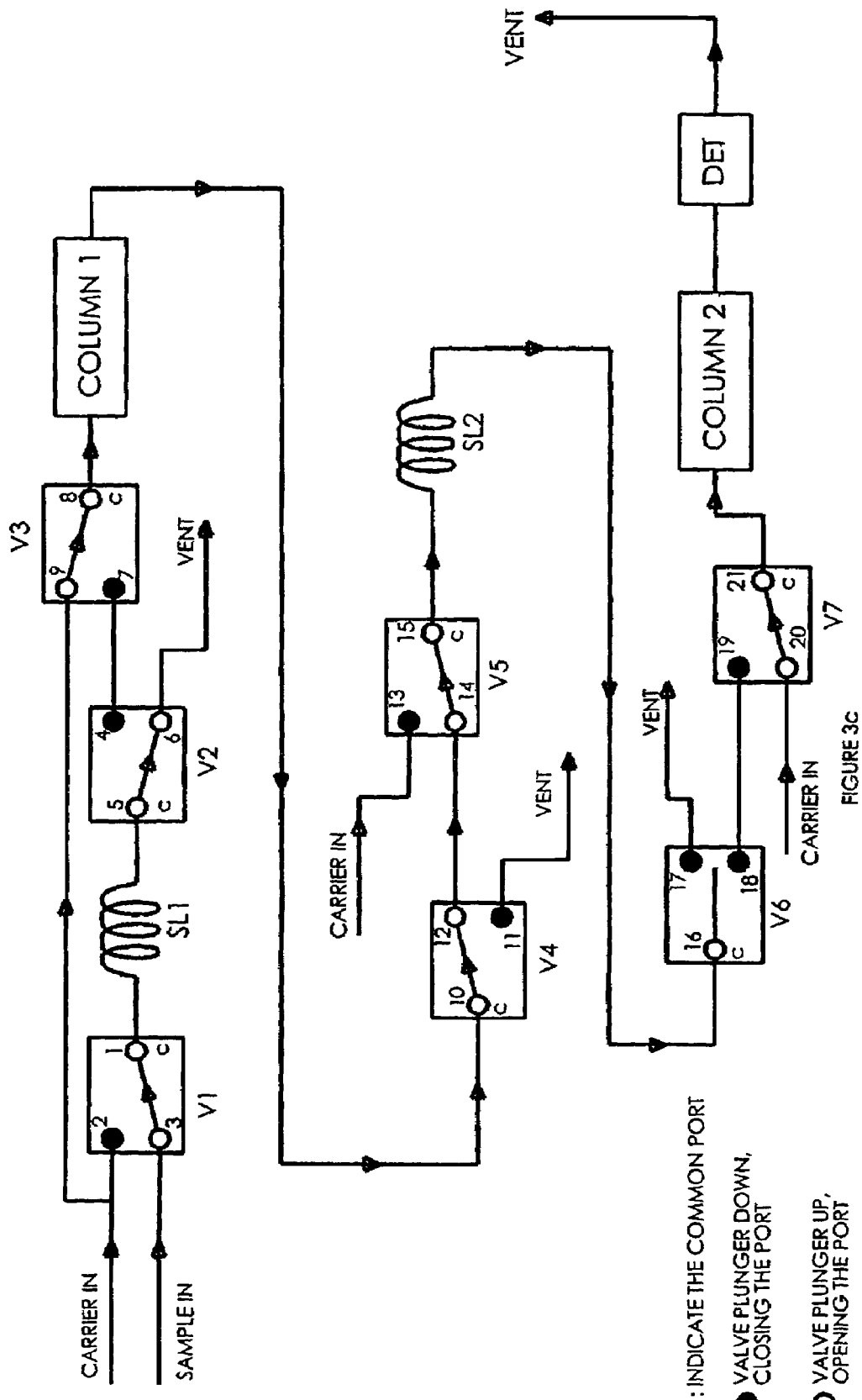
FIG. 3c is another schematic representation of the analytical chromatographic system shown in FIG. 3a, the system being in a third position.
Figure 3D:
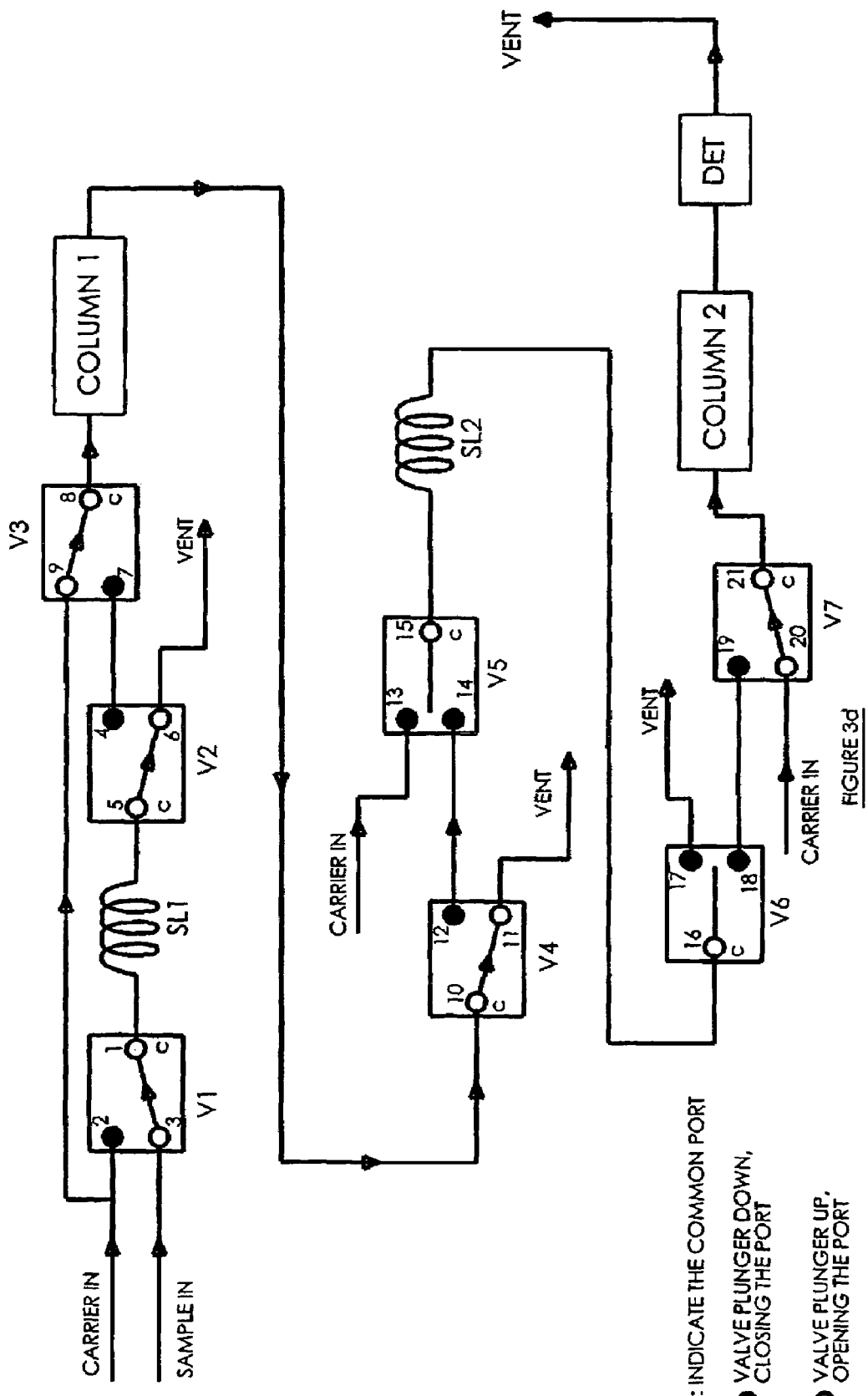
FIG. 3d is another schematic representation of the analytical chromatographic system shown in FIG. 3a, the system being in a fourth position.
Figure 3E:
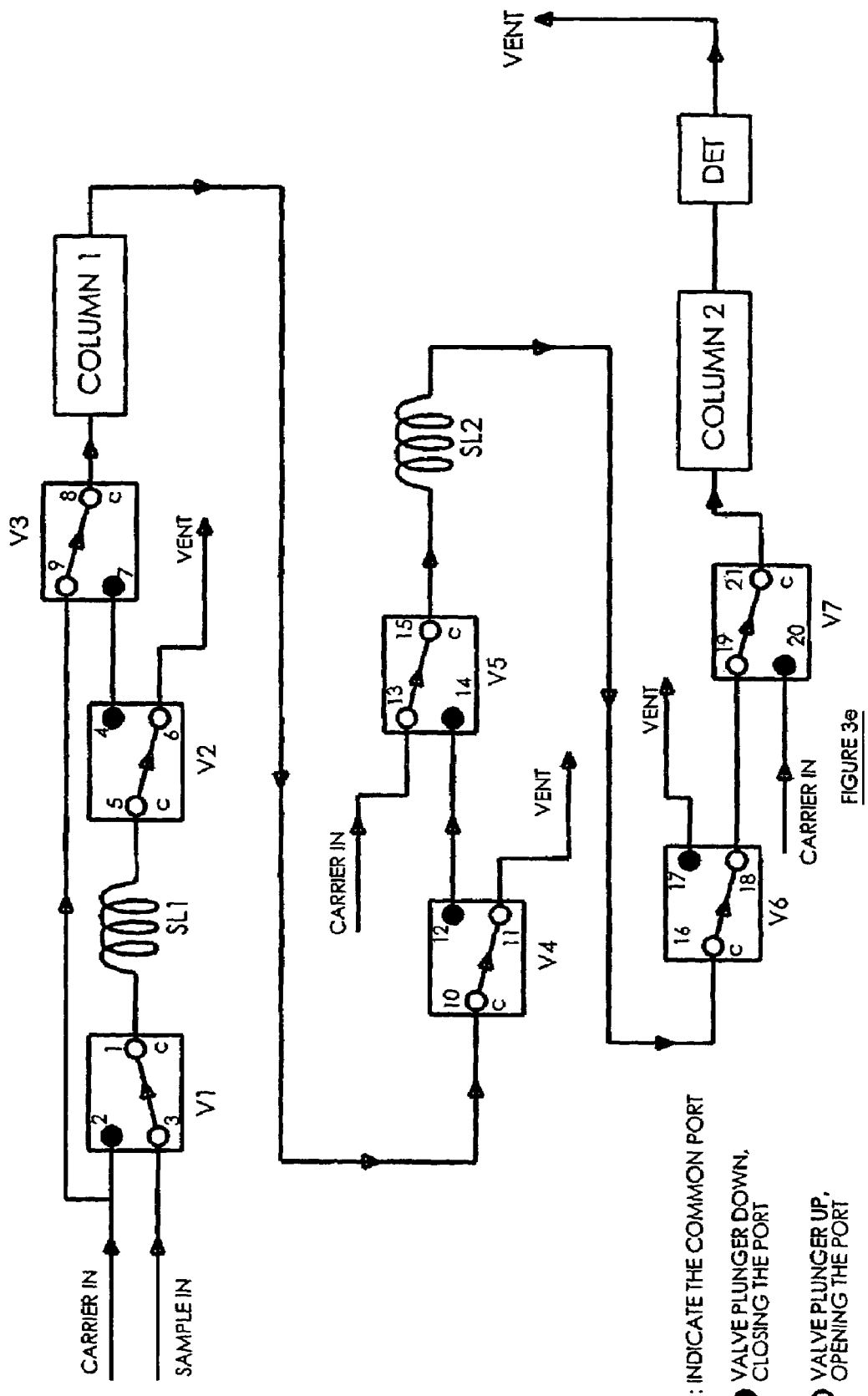
FIG. 3e is another schematic representation of the analytical chromatographic system shown in FIG. 3a, the system being in a fifth position.
Figure 3F:
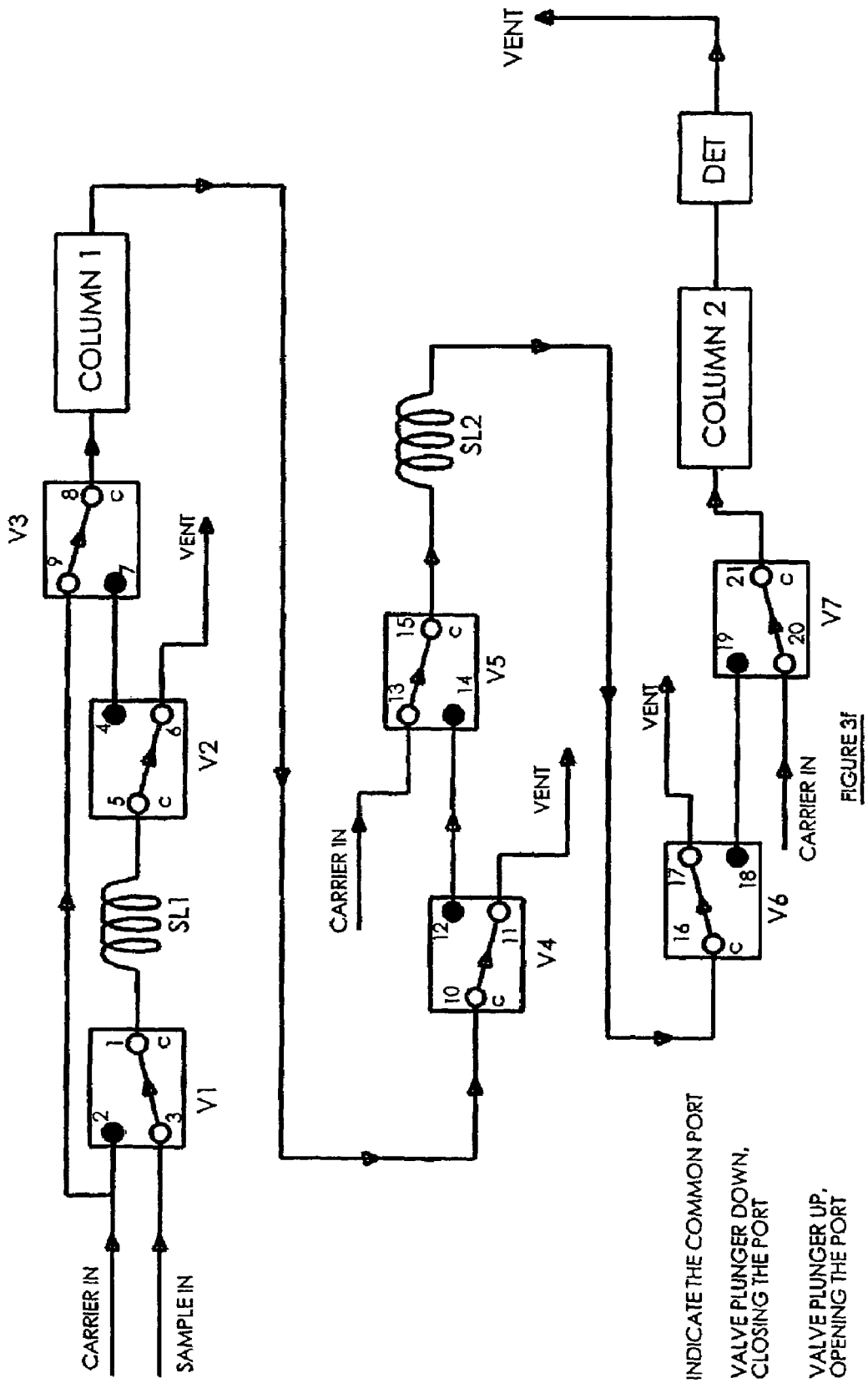
FIG. 3f is another schematic representation of the analytical chromatographic system shown in FIG. 3a, the system being in a sixth position.

Referring now to FIG. 3f, the second sample loop SL2 is initially purged with the carrier gas and depressurized at atmospheric pressure. For this purpose, the second sample loop SL2 is provided with the carrier gas for purging it through a second loop venting line. The second sample loop SL2 is then isolated by actuating the valves V5 and V6, as illustrated in FIG. 3a. Preferably, when isolated, the second sample loop SL2 has a carrier gas volume at atmospheric pressure therein. During this time, the second separation column 2 is advantageously provided with the carrier gas passing therethrough. In other words, the second separation column 2 is swept by the carrier gas.

Referring now to FIG. 3a, the first sample loop SL1 is provided with the gas sample for filling the first sample loop SL1 with a gas sample volume. To this end, the valves V1 and V2 are conveniently actuated. Once the first sample loop SL1 is filled, the gas sample volume is injected into the first separation column 1 to substantially separate the gas background from the impurities, as illustrated on FIG. 3b. The valves V1 to V3 are conveniently actuated to perform this gas sample volume injection. At the same time, the first separation column 1 is vented outside the system through a first column vent line for a predetermined venting period of time for eliminating at least a part of the gas background. This is done through the valve V4.

When most of the gas background, H2 for example, is vented away from the first separation column 1 through the valve V4, and just before the impurities peak of interest, O2 peak for example, is coming out of the first separation column 1, the valves V4 and V5 are switched in the position shown in FIG. 3c. In this position, the first separation column 1 is then connected to the second sample loop SL2 during a predetermined filling period of time for filling the second sample loop SL2 with a gas mixture comprising a carrier gas volume and a slice of the gas sample volume comprising at least one of the impurities. Preferably, each of the predetermined periods of time is particularly determined so that the slice of the gas sample volume comprises at least one of the impurities of interest. More preferably, each of the predetermined periods of time is particularly determined so that the slice of the gas sample volume has a width substantially corresponding to a corresponding peak width of a corresponding one of the impurities. In other words, the O2 peak and a part of the H2 sample background preferably begin to fill the second sample loop SL2. This step begins just before T3 in the chromatograph of FIG. 4. After that, preferably at T4, the valves V4 and V5 are switched to the position shown in FIG. 3d. In this position, the second sample loop SL2 is isolated and filled with an O2 impurity of the sample, a part of H2 sample background and the carrier gas. All this gives a homogeneous mixture.

Figure 1:
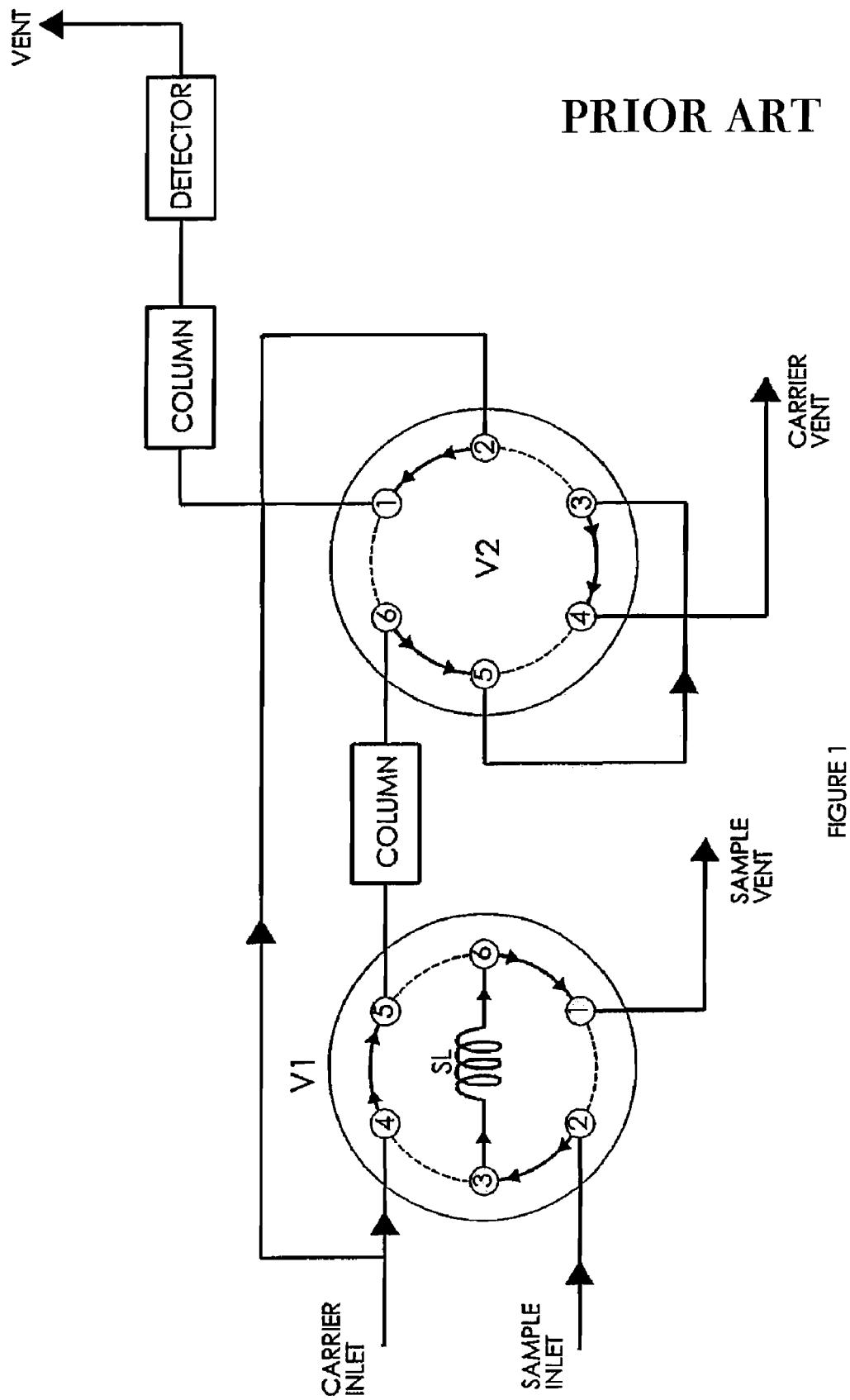
FIG. 1 (PRIOR ART) is a schematic representation of a typical analytical chromatographic system known in the art.

Referring now to FIG. 3e, the gas mixture is then injected into the second separation column 2 to separate the gas mixture into a plurality of baseline resolved peaks, thereby allowing to measure the at least one of the impurities. When measuring O2 in H2, a clean separation of H2 and O2 is obtained. Indeed, most of the H2 background has been replaced by the carrier gas, while leaving the O2 impurities unaffected. Moreover, advantageously, there is no peak tailing since all of the gas mixture of the second sample loop SL2 is quickly injected into the second separation column 2 instead of being slowly transferred from the first separation column 1 like in the traditional heartcut method shown in FIG. 1. To inject the gas mixture into the second separation column 2, the valves V5, V6 and V7 are switched to the position shown in FIG. 3e.

Then, as mentioned above, in order to start another cycle, the second sample loop SL2 is depressurized and isolated to start another cycle. A quick purge of the second sample loop with the carrier gas is shown in FIG. 3f. Then, the valve V5 is closed, i.e. both ports are closed, and then the ports of the valve V6 are closed. Thus, in this position, the second sample loop SL2 is advantageously purged with the clean carrier gas while its volume is advantageously set at atmospheric pressure.

In a further preferred embodiment, the chromatographic method may further comprise, after the step g) of connecting the first column 1 to the second sample loop SL2, a step of repeating each of the previous steps f) and g) for filling the second sample loop SL2 with the sample mixture. The sample mixture then comprises a plurality of slices of the gas sample volume, each of the slices comprising a single one of the impurities. Preferably, for each of the iterations of the steps f) and g), each of the predetermined periods of time is particularly determined so that each of the slices of the gas sample volume has a width substantially corresponding to a corresponding peak width of the corresponding one of the impurities. In other words, each impurities peak of the chromatogram shown in FIG. 4, could advantageously be transferred individually into the second sample loop SL2 and injected into the second separation column 2 to get a clean separation and provide baseline resolved peaks. However, as it will be more detailed thereinafter, it is preferable to transfer only peaks that are affected by the sample background.

Figure 5:
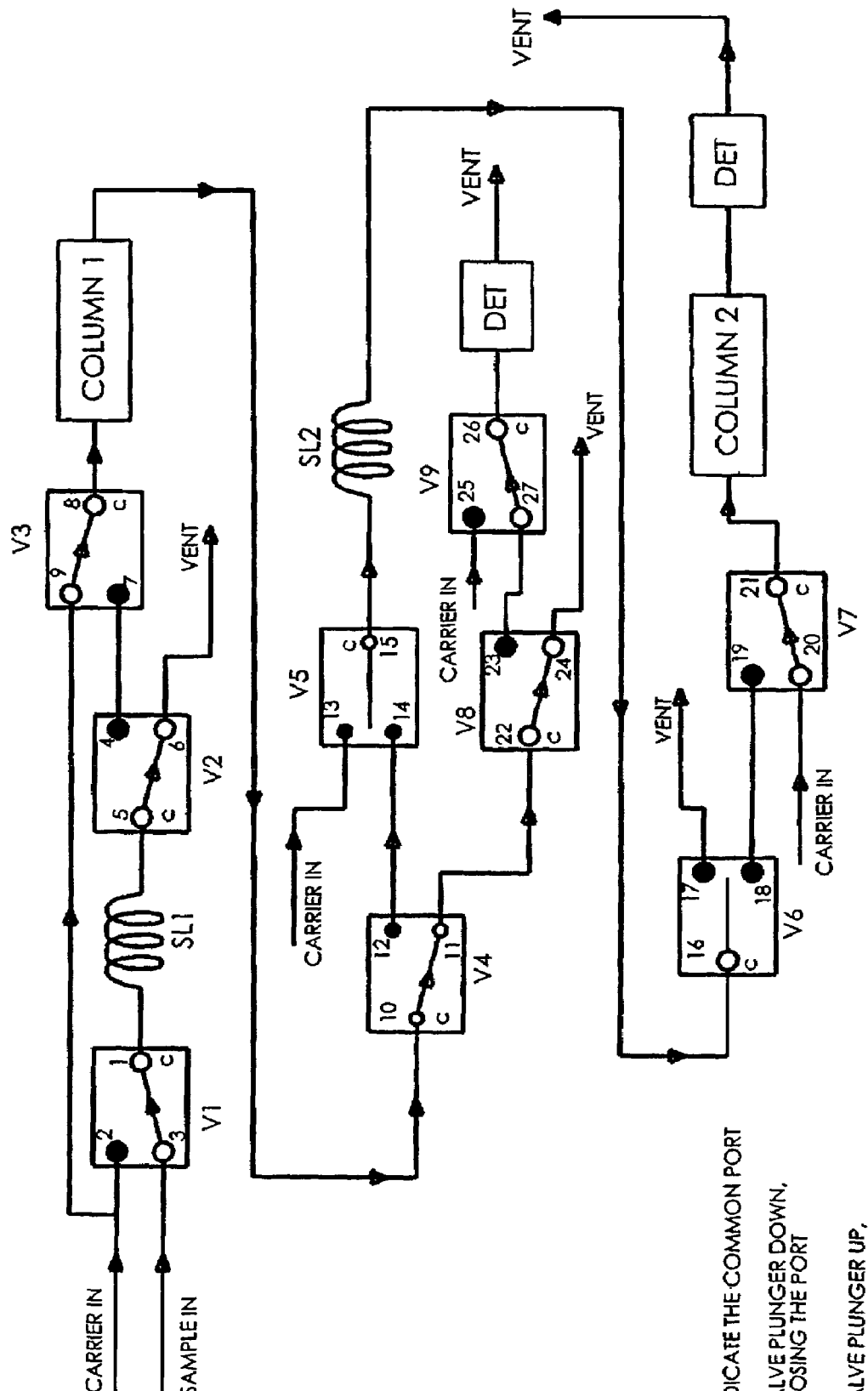
FIG. 5 is a schematic representation of another analytical chromatographic system, according to a further preferred embodiment of the present invention.

Referring now to FIG. 5, there is shown another further preferred embodiment of the present invention which is particularly advantageous to improve the analysing cycle time. The illustrated system is advantageously further provided with an additional detector operatively connectable to the first separation column 1 through a plurality of additional valves VB and V9. The method further comprises, after the step g) of connecting the first separation column 1 to the second sample loop SL2, an additional step of connecting the first separation column 1 to the additional detector for measuring the remaining impurities of the gas sample with the additional detector. In fact, the valves VB and V9 allow the process to keep the additional detector swept by the carrier gas while the gas background, H2 for example, is vented away. When the impurities peak of interest, the O2 peak for example, has been transferred, the valve V4 is set back in the position shown in FIG. 3d. The balance of the peaks shown in the chromatogram of FIG. 4, i.e. the remaining impurities, or in other words, the peaks eluting after O2, could then advantageously be processed by the additional detector since there is not enough gas background, H2 for example, to interfere with them. This advantageously reduces the total cycle time required to analyze a process sample.

It is worth mentioning that this method could also advantageously be used for other gas backgrounds like N2, O2, etc. People well versed in the art will understand that only a re-timing of the valves sequence would thus be required.

In a further preferred embodiment which is not illustrated, each of the first and second sample loops SL1 and SL2, respectively, has a first and a second sample loop volume. The first sample loop volume is preferably smaller than the second sample loop volume. Each of the first and second separation columns 1, 2, respectively, has a first and a second column volume. The first column volume is preferably smaller than the second column volume for allowing the process to limit a pressurization of the second sample loop SL2 during the step g) of connecting the first column 1 to the second sample loop SL2 for transferring the peak of interest into it.

However, when the peak duration is long, the transfer time to the second sample loop SL2 will also be longer. In this case, the vented side of the second sample loop SL2 could advantageously be directed to a variable volume. This volume will expand in order to keep the second sample loop pressure at atmospheric pressure. So it will keep the gas carrier flow in the first separation column 1 constant when filling the second sample loop SL2.

Figure 7:
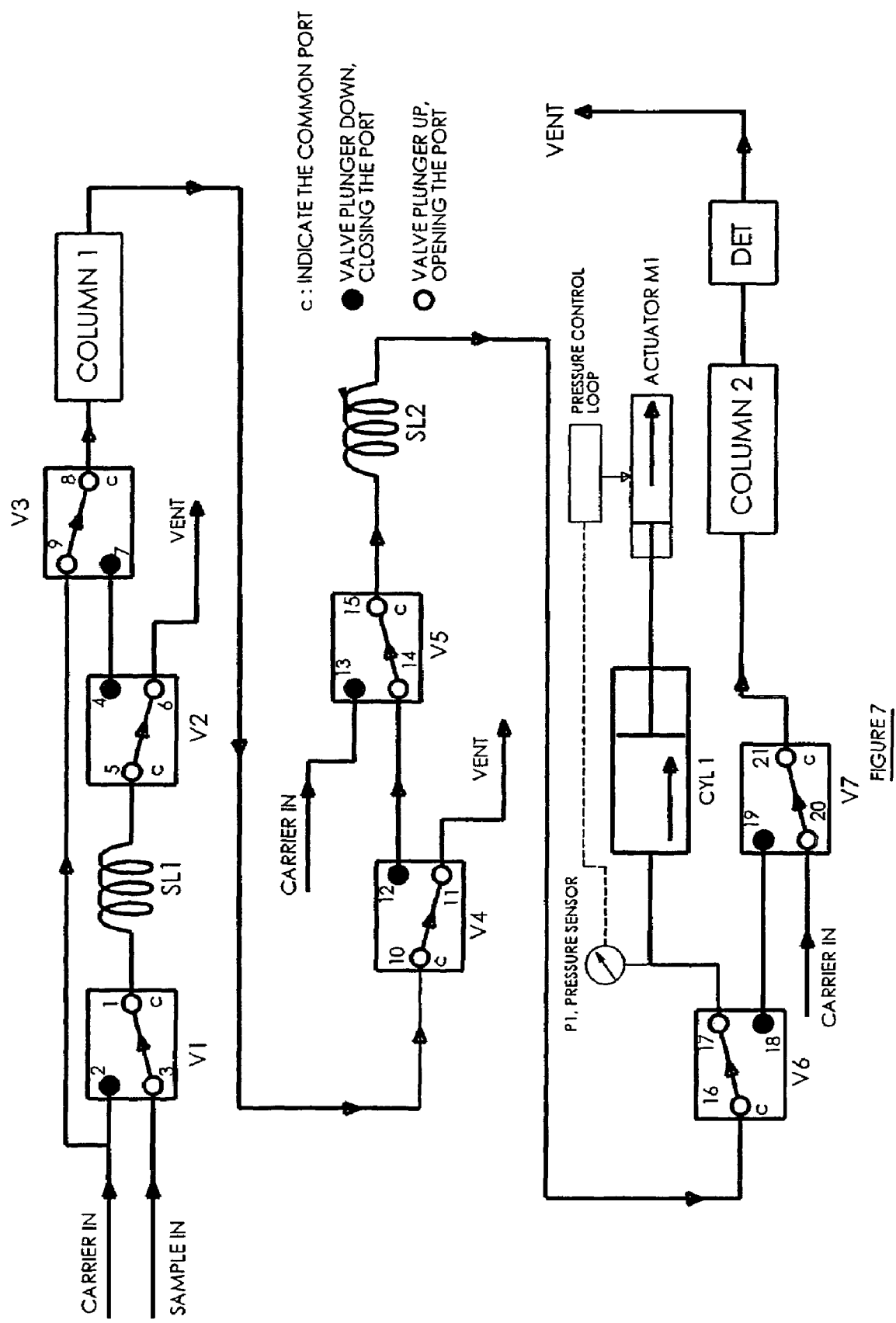
FIG. 7 is a schematic representation of another analytical chromatographic system, according to a further preferred embodiment of the present invention.
Figure 8:
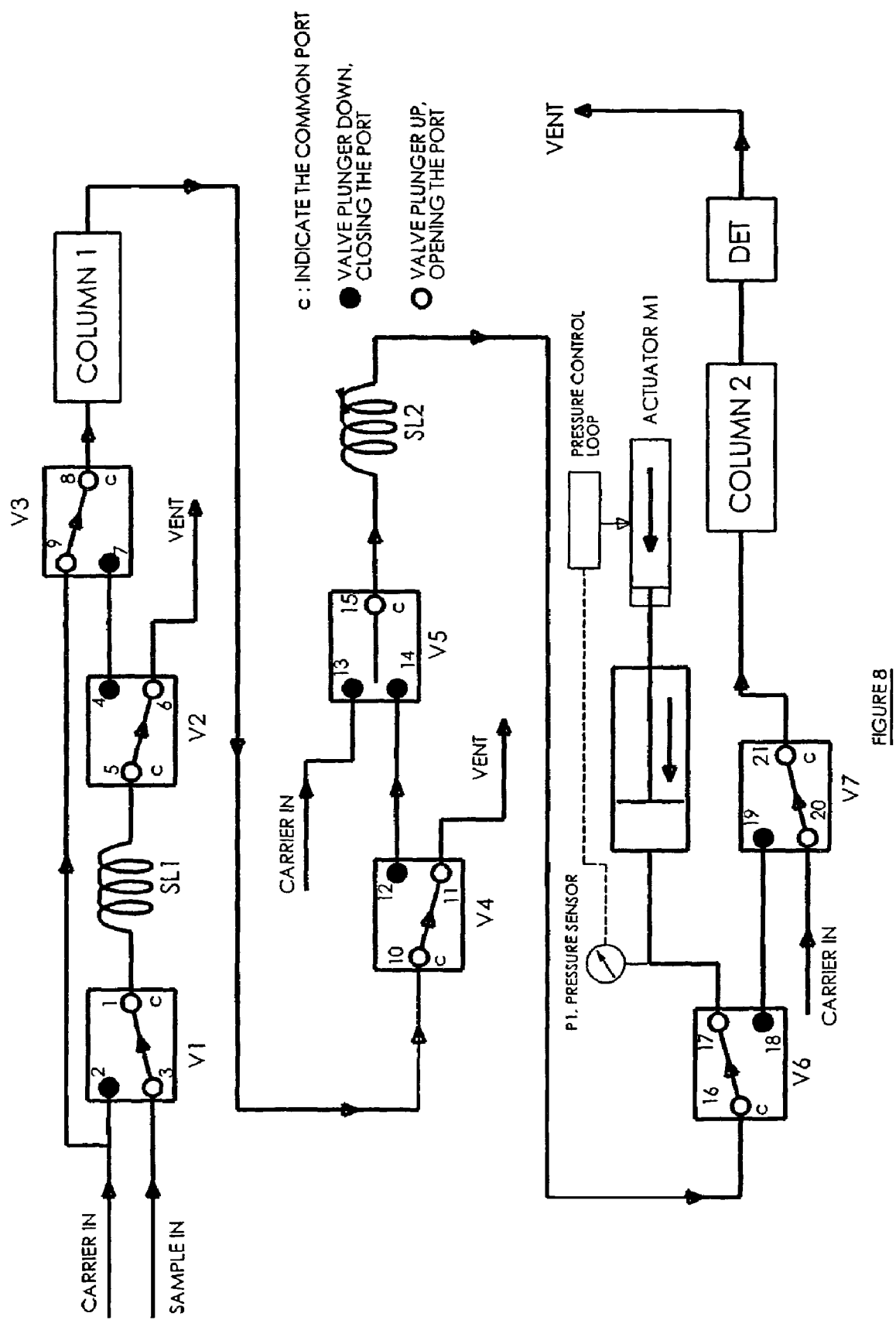
FIG. 8 is another schematic representation of the system of FIG. 7, the system being in another position.

FIGS. 7 and 8 illustrate such a configuration. In fact, the second sample, loop SL2 is provided with an additional variable volume. The method further comprises, during the step g) of connecting the first separation column 1 to the second sample loop SL2, the following additional steps. The first column gas pressure is firstly measured. The variable volume is then expanded during the filling of the second sample loop SL2 according to the first column gas pressure in order to keep constant the gas pressure, preferably at atmospheric pressure. After that and before the step h) of isolating the second sample loop SL2, the inlet of the second sample loop SL2 is isolated. Then, the variable volume is reduced to pressurize the second sample loop SL2.

As illustrated, the variable volume can advantageously be a gas tight cylinder CYL1. Of course, any other convenient means providing a variable volume could be envisaged.

In this configuration, when the impurities peak to be extracted is about to come out of the first separation column 1, the outlet of column 1 is then switched to allow it to flow so it can go through the second sample loop SL2 with the help of the valves V4 and V5. At the same time, the valve V6 is switched to allow the gas mixture of the second sample loop SL2 to go into the variable volume cylinder CYL1. In this configuration, the idea is to advantageously maintain the outlet pressure of the first separation column 1 as the atmospheric pressure in order to keep its flow constant. To achieve this, the pressure sensor PI measures the system pressure and sends this information to a pressure control loop. The pressure control loop sends a signal to a motor M1. The motor M1 begins to turn to move the piston of the cylinder CYL 1 out. This allows the cylinder CYL 1 internal volume to expand while advantageously keeping the outlet pressure of the second sample loop and of the first separation column 1 constant. When all the peaks of interest have finished coming out of the first separation column 1, the first column's outlet is switched back to vent through the valve V4. The inlet of the second sample loop SL2 is then isolated by loosing both ports 13 and 14 of the valve V5.

At this time, the control loop reverses the direction of the motor M1 to push back the piston of the cylinder CYL 1 inward. This step will move the accumulated volume of gas in the cylinder CYL 1 into the second sample loop SL2 and tubing connected to it. This has for effect to pressurize the second sample loop SL2. Indeed, all of the gas volume in the cylinder CYL1 is practically reduced to zero when the piston is pushed back completely inside the cylinder CYL1.

Since the tubing volume connecting the outlet of the second sample loop SL2 to the cylinder CYL 1 is very small, most of the previously accumulated gas volume of the cylinder CYL 1 has been transferred back into the second sample loop SL2 by pressurization. There is of course a very little volume of gas that stays out of the second sample loop SL2 after this step. Since this volume is always the same, it does not have any detrimental effect on the final measurement results because this is repeatable from cycle to cycle having the same timing parameter. When the pressurization of the second sample loop SL2 is done, the port 17 of the valve V6 is closed. At this time, the gas mixture into the second sample loop SL2 is ready to be injected into the second separation column 2.

In another further preferred embodiment, the method advantageously provides the possibility of concentrating an impurities peak by collecting two or more of it before injecting the gas mixture of the second sample loop SL2 into the second separation column 2. This could be achieved by filling the second sample loop SL2 with the same impurities peak two times or more before injecting it into the second separation column 2. Thus, in this embodiment, before the step h) of isolating the second sample loop SL2, each of the above-identified steps d) to g) are sequentially performed a plurality of times for collecting a plurality of slices of the gas sample volume comprising the at least one of the impurities.

Thus, in this case, the resulting peak will advantageously have two or more times the height of a single one. Then, the sensitivity of the analytical system is advantageously increased by two or more, depending on the number of times the second sample loop is filled with the same impurities peak.

Another advantageous application of this method is the measurement of argon in O2. Indeed, the problems mentioned-above become even worst when the impurities of interest are not separated from the background without using extreme operating conditions. This is the case when trying to measure argon in oxygen with a chromatographic technique. In this case, both the argon and oxygen co-elute. Various groups have proposed solutions to do this measurement. For example, U.S. Pat. No. 5,762,686 shows a system based on a pressure swing adsorption process used in combination with a gas chromatograph. This solution is quite complex and not practical in a process control application. It requires extensive data manipulation and requires at least two cycles to get the argon value.

There is also U.S. Pat. No. 4,747,854 which describes a method of ion exchange of a standard zeolite that allows to separate argon and oxygen with normal operating conditions. However, in an oxygen sample, there is also Nitrogen. The retention time for nitrogen in a six foot long ⅛"O.D. column is about one hour when using this ion exchange zeolite. Furthermore it appears that the Ar/O2 separation is affected over time by the moisture contained in the sample.

Some other users use a de-oxo to remove oxygen totally from the sample. Depending on the sample volume, the de-oxo must be regenerated with H2 almost every sixteen hours. This system is also quite complex since valves, purge gas and H2 are required. In the art, the Valco's company proposes such a de-oxo system.

The peak slicing method of the present invention which will be more detailed below could advantageously be used to extract the argon peak from bulk oxygen and re-inject it through an O2 trap to get the argon peak. Since most of the O2 background is replaced with carrier gas, the trap life is extended.

Figure 6:
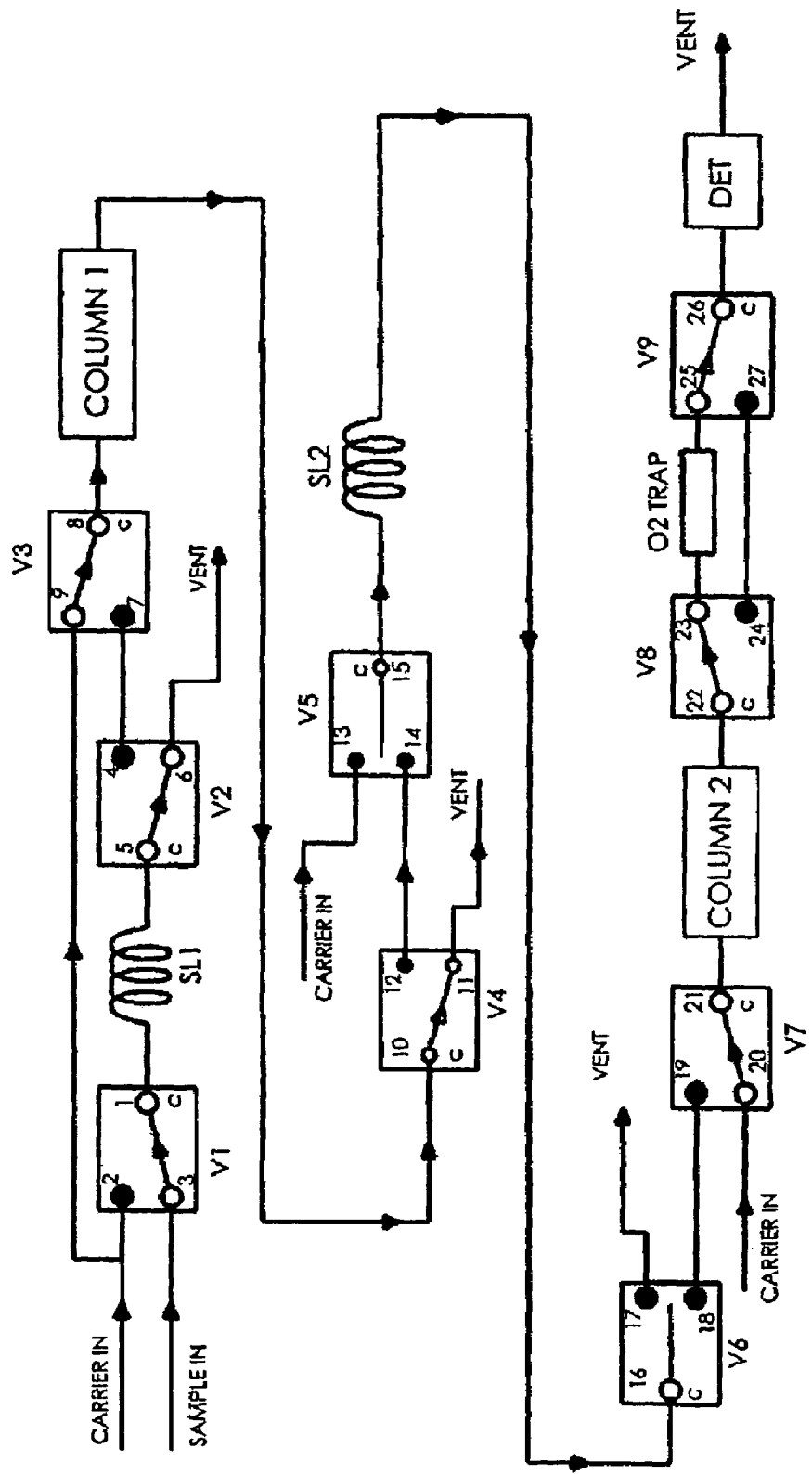
FIG. 6 is a schematic representation of another analytical chromatographic system, according to a further preferred embodiment of the present invention.

FIG. 6 illustrates a further preferred embodiment of the analytical system of the present invention which can advantageously be used to implement the peak slicing method, particularly useful for the measurement of argon in O2. In fact, this system is the same as the one illustrated in FIGS. 3a to 3f but the valves VB, V9 and an O2 trap have been added after the second separation column 2. The O2 trap is operatively connectable between the second separation column 2 and the detector through the valves VB and V9. When the step i) of injecting the gas mixture in the second separation column 2 has been performed, the O2 trap is operatively connected between the second separation column 2 and the detector during a predetermined period of time for trapping oxygen therein while providing the detector with a slice of the gas mixture comprising the argon impurities. In other words, the valves VB and V9 are conveniently actuated to put the O2 trap in circuit only when the argon peak comes out of the second separation column 2. A proper timing of the valves VB and V9 in such way of opening a window only for the argon peak, will also contribute to reject some of the balance of oxygen in the sample. The O2 trap will advantageously absorb the trace of O2, and the argon peak will go through unaffected. The result is a clean baseline resolved argon peak. When switching back the valves VB and V9 to by-pass and isolate the O2 trap, other impurities could be measured, without passing them through the trap. It is worth mentioning that in the present description, by the expression "O2 trap", it is meant any convenient means that would allow to trap oxygen therein, or any convenient means which would allow to separate argon and oxygen from each other.

Typically, a copper base catalyst used to make the O2 trap will advantageously work over nine months before requiring regeneration. This is based on one injection every five minutes, twenty-four hours/day. Level as low as ppb argon was easily measured in 100% of O2. This is a net improvement compared to existing system. Nevertheless, it is worth mentioning that the success of these methods relies on valve performance in terms of leak, port sealing and dead volume effect. Therefore, the above mentioned diaphragm sealed valve of the present inventors can advantageously be used, even if other suitable valves could be envisaged.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

What is claimed is:

1. A chromatographic method for measuring impurities in a gas sample having a gas background, said method comprising the steps of:
    a) providing a chromatographic system having a first sample loop, a first separation column, a second sample loop, a second separation column and a detector serially connected through a plurality of valves, said system being provided with a carrier gas and the gas sample;
    b) providing the second sample loop with the carrier gas for purging said second sample loop through a second loop venting line;
    c) isolating said second sample loop;
    d) providing said first sample loop with the gas sample for filling said first sample loop with a gas sample volume;
    e) injecting said gas sample volume into said first column to substantially separate the gas background from the impurities;
    f) venting said first column outside the system through a first column vent line for a predetermined venting period of time for eliminating at least a part of the gas background;
    g) connecting said first column to said second sample loop during a predetermined filling period of time for filling said second sample loop with a gas mixture comprising a carrier gas volume and a slice of the gas sample volume comprising at least one of said impurities;
    h) isolating said second sample loop; and
    i) injecting said gas mixture into the second column to separate the gas mixture into a plurality of baseline resolved peaks, thereby allowing measurement of the at least one of said impurities.

2. The chromatographic method according to claim 1, wherein said impurities comprise oxygen and said gas background comprises argon.

3. The chromatographic method according to claim 1, wherein said impurities comprise argon and said gas background comprises oxygen.

4. The chromatographic method according to claim 1, wherein said impurities comprise oxygen and said gas background comprises hydrogen.

5. The chromatographic method according to claim 1, wherein each of said valves comprises a three-way valve having independently actuated ports and providing a tight shut-off of said ports.

6. The chromatographic method according to claim 1, wherein in step c), said second sample loop has a carrier gas volume at atmospheric pressure therein.

7. The chromatographic method according to claim 1, further comprising before step i) a step of providing the second separation column with the carrier gas passing therethrough.

8. The chromatographic method according to claim 1, wherein each of said predetermined periods of time is particularly determined so that the slice of the gas sample volume comprises at least one of said impurities.

9. The chromatographic method according to claim 1, wherein each of said predetermined periods of time is particularly determined so that the slice of the gas sample volume has a width substantially corresponding to a corresponding peak width of a corresponding one of said impurities.

10. The chromatographic method according to claim 1, further comprising after step g), a step of repeating each of said steps f) and g) for filling said second sample loop with said sample mixture, the sample mixture comprising a plurality of slices of the gas sample volume, each of said slices comprising a single one of said impurities.

11. The chromatographic method according to claim 10, wherein for each iteration of the steps f) and g), each of the predetermined periods of time is particularly determined so that each of said slices of the gas sample volume has a width substantially corresponding to a corresponding peak width of the corresponding one of said impurities.

12. The chromatographic method according to claim 1, wherein the chromatographic system is further provided with an additional detector operatively connectable to the first separation column through a plurality of additional valves, the method further comprising after step g) an additional step of connecting said first separation column to said additional detector for measuring the remaining impurities of said gas sample with said additional detector, thereby providing a reduced analysing cycle time of said gas sample.

13. The chromatographic method according to claim 12, further comprising, after step g), a step of providing the additional detector with the carrier gas passing therethrough.

14. The chromatographic method according to claim 1, wherein each of said first and second sample loops respectively has a first and a second sample loop volume, the first sample loop volume being smaller than the second sample loop volume, each of said first and second separation column respectively has a first and a second column volume, the first column volume being smaller than the second column volume for allowing to limit a pressurization of said second sample loop during step g).

15. The chromatographic method according to claim 1, wherein said second sample loop is provided with an additional variable volume, the method further comprising, during said step g), additional steps of:
   measuring a first column gas pressure; and
   expanding said variable volume during filling of the second sample loop according to said first column gas pressure in order to keep constant said gas pressure;
and wherein the method further comprises before said step h) additional steps of:
   isolating an inlet of said second sample loop; and
   reducing said variable volume for pressurizing said second sample loop.

16. The chromatographic method according to claim 15, wherein during said step of expanding said variable volume, said first column gas pressure is kept at atmospheric pressure.

17. The chromatographic method according to claim 1, wherein before step h), each of steps d) to g) are sequentially performed a plurality of times for collecting a plurality of slices of the gas sample volume comprising said at least one of said impurities.

18. The chromatographic method according to claim 1, wherein said impurities comprise argon and said gas background comprises oxygen, the system being further provided with an O2 trap operatively connectable between said second separation column and said detector through a first and a second additional valves, the method further comprising, after step i), an additional step of:
   j) operatively connecting said O2 trap between said second column and said detector during a predetermined period of time for trapping oxygen therein while providing said detector with a slice of said gas mixture comprising said argon impurities.

* * * * *

UNITED STATES PATENT AND TRADEMARK OFFICE
CERTIFICATE OF CORRECTION

PATENT NO. : 7,451,634 B2
APPLICATION NO. : 11/361068
DATED : November 18, 2008
INVENTOR(S) : Yves Gamache et al.

It is certified that error appears in the above-identified patent and that said Letters Patent is hereby corrected as shown below:

Title page:

Item [73] Please replace "Systeme Analytique, Inc." with --Panalytique Inc.--

Signed and Sealed this

Eighth Day of September, 2009

David J. Kappos
*Director of the United States Patent and Trademark Office*